US012616824B2

(12) United States Patent
   Gao et al.

(10) Patent No.: US 12,616,824 B2
(45) Date of Patent: May 5, 2026

(54) HEAT-RESISTANT IMPLANTABLE POLYMER MICRONEEDLE AND PREPARATION METHOD THEREFOR AND APPLICATION THEREOF

(71) Applicant: TECHNICAL INSTITUTE OF PHYSICS AND CHEMISTRY OF THE CHINESE ACADEMY OF SCIENCES, Beijing (CN)

(72) Inventors: Yunhua Gao, Beijing (CN); Xiaoyu Zhao, Beijing (CN); Suohui Zhang, Beijing (CN)

(73) Assignee: TECHNICAL INSTITUTE OF PHYSICS AND CHEMISTRY OF THE CHINESE ACADEMY OF SCIENCES, Beijing (CN)

( * ) Notice: Subject to any disclaimer, the term of this patent is extended or adjusted under 35 U.S.C. 154(b) by 814 days.

(21) Appl. No.: 17/927,445

(22) PCT Filed: Jun. 4, 2021

(86) PCT No.: PCT/CN2021/098279
   § 371 (c)(1),
   (2) Date: Nov. 23, 2022

(87) PCT Pub. No.: WO2021/244630
   PCT Pub. Date: Dec. 9, 2021

(65) Prior Publication Data
   US 2023/0173241 A1     Jun. 8, 2023

(30) Foreign Application Priority Data
   Jun. 4, 2020   (CN) .......................... 202010499541.9

(51) Int. Cl.
   *A61M 37/00*     (2006.01)
   *C08L 1/02*      (2006.01)
   *C08L 39/06*     (2006.01)

(52) U.S. Cl.
   CPC ........... *A61M 37/0015* (2013.01); *C08L 1/02* (2013.01); *C08L 39/06* (2013.01); (Continued)

(58) Field of Classification Search
   CPC ....... A61M 37/0015; A61M 2037/0046; C08L 1/02; C08L 39/06; C08L 2201/06 (Continued)

(56) References Cited

FOREIGN PATENT DOCUMENTS

| CN | 106659876 | 5/2017 |
| CN | 110448541 | 11/2019 |

(Continued)

OTHER PUBLICATIONS

International Search Report (English and Chinese) and Written Opinion of PCT/CN2021/098279 dated Sep. 8, 2021, 12 pages.

*Primary Examiner* — Phillip A Gray
(74) *Attorney, Agent, or Firm* — Rankin, Hill & Clark LLP

(57) ABSTRACT

Disclosed are a heat-resistant implantable polymer microneedle and a preparation method therefor and an application thereof. The microneedle comprises a needle tip, a needle body, and a base, wherein the needle tip comprises a homogeneous system formed by mixing a biodegradable macromolecular material which has a glass transition temperature of 35-65° C. and is difficultly soluble in water and a macromolecular material having a glass transition temperature higher than that of the biodegradable macromolecular material. The microneedle has good heat resistance and puncture property.

16 Claims, 3 Drawing Sheets

(52) U.S. Cl.
CPC .. *A61M 2037/0046* (2013.01); *C08L 2201/06*
(2013.01); *C08L 2203/02* (2013.01)

(58) Field of Classification Search
USPC ........................................................ 604/173
See application file for complete search history.

(56)                    References Cited

FOREIGN PATENT DOCUMENTS

| | | | | |
|---|---|---|---|---|
| CN | 110882209 | 3/2020 | | |
| WO | 2019094349 | 5/2019 | | |
| WO | WO-2019094349 A1 * | 5/2019 | ........ | A61M 37/0015 |

* cited by examiner

HEAT-RESISTANT IMPLANTABLE POLYMER MICRONEEDLE AND PREPARATION METHOD THEREFOR AND APPLICATION THEREOF

TECHNICAL FIELD

The present application relates to the technical field of medicines, in particular to a heat-resistant implantable polymer microneedle, a preparation method therefor, and an application thereof.

BACKGROUND

Transdermal drug delivery refers to drug delivery implemented via skin. The capillaries in the skin absorb the drug into the blood circulation system to play a therapeutic role. The transdermal drug delivery can avoid the "first pass effect" to release the drug steadily and slowly, thus improving the bioavailability of the drug. Moreover, patients can take the drug by themselves, achieving good compliance. However, due to the barrier of the stratum corneum, the drug penetration efficiency is not high, and the types of drugs for transdermal drug delivery are very limited. The microneedle is a new type of transdermal drug delivery, and is composed of sharp micro protrusion arrays. The microneedle can puncture the stratum corneum to form a micro drug delivery channel on the skin and release the drug to a target cortex. Therefore, the microneedle can overcome the barrier of the stratum corneum, significantly improving transdermal drug penetration efficiency and enriching the types of drugs for transdermal penetration, and thus is a minimally invasive and painless drug delivery way.

Currently, there are many kinds of materials for preparing microneedles, such as silicon, glass, metals, and polymers. However, a microneedle made of silicon or glass is brittle and easy to break under an external force, making it inconvenient to use. A metal microneedle has relatively good mechanical strength but requires a high cost and a complicated preparation process and thus is inapplicable to large-scale production. A polymer microneedle has good mechanical strength and requires a low cost and a simple preparation process and thus is applicable to large-scale production of microneedles. The materials for preparing the polymer microneedle include: water-soluble polymers, swelling polymers, and biodegradable polymers. These polymers all have good biocompatibility and a specific degradation mode or swelling property, and a drug release behavior can be effectively controlled according to the properties of the polymer materials. Polylactic acid macromolecular materials have excellent biocompatibility and biodegradability and good mechanical properties, and are ideal materials for preparing biodegradable polymer microneedles. Drug-loaded polymer microneedles, which are prepared using polylactic acid as sustained-release materials, are widely applied in the field of transdermal drug release.

Polylactic acid microneedles are widely applied in transdermal drug sustained-release, and storage conditions thereof are problems frequently considered in the field of preparations, wherein the temperature is an important factor that affects the stability of the microneedles. The glass transition temperature is a temperature for transition of an amorphous polymer from a glassy state to a high elastic state, and is an important index for measuring the heat resistance of the polymer. When the external temperature is close to or higher than the glass transition temperature of the polymer, the polymer microneedle melts and deforms, making the microneedle useless. Document 1 (Plastics Industry. 2012 January; 40(1):68-71.) and Document 2 (J Control Release. 2017 March; 249:11-22.) reported that the glass transition temperatures of polylactic acid (PLA), polyglycolic acid (PGA), and polylactic-glycolic acid (PLGA) are respectively 40-60° C., 35-40° C., and 40-60° C. These macromolecular materials have relatively low glass transition temperatures, resulting in poor heat resistance of the microneedles made therefrom. For example, after a microneedle prepared by using PLGA as a tip material stands at 40° C. for two days, the tip of the microneedle melts into a sphere, as shown in FIG. 1. Accordingly, there are great difficulties in the storage and use of polylactic acid microneedles at high temperatures. Therefore, it is necessary to provide a heat-resistant implantable polylactic acid microneedle to facilitate storage and use in summer or tropical areas.

BRIEF SUMMARY

In view of the defects in the prior art, the first objective of the present application is to provide a heat-resistant implantable polymer microneedle.

The second objective of the present application is to provide a method for preparing a heat-resistant implantable polymer microneedle, the method having a simple process and a low cost.

The third objective of the present application is to provide a microneedle patch, the microneedle patch having good heat resistance.

The fourth objective of the present application is to provide use of the microneedle patch.

In order to achieve the first objective, the present application adopts the following technical solution:

A heat-resistant implantable polymer microneedle includes a needle tip, a needle body, and a base.

The needle tip includes a homogeneous system formed by mixing a biodegradable macromolecular material A which has a glass transition temperature of 35-65° C. and is difficultly soluble in water and a macromolecular material B having a glass transition temperature higher than that of the biodegradable macromolecular material.

That is, the needle tip includes the homogeneous system formed by mixing the biodegradable macromolecular material A which is difficultly soluble in water and the macromolecular material B, wherein the glass transition temperature of the biodegradable macromolecular material A is 35-65° C., and the glass transition temperature of the macromolecular material B is higher than that of the biodegradable macromolecular material A.

In an example, in the microneedle, the needle tip is located on the needle body and the needle body is located on the base. The needle body and the base can be an integrated structure, or can be independent structures.

In an example, the height of the needle tip does not exceed two-thirds of the overall height of the microneedle, preferably does not exceed one-half. In this solution, the needle tip is not prone to drawing-out during peeling-off of a base membrane after the microneedle is stuck into skin, so that the needle tip can be completely left under the skin as a drug repository.

In an example, a structure formed by the needle tip and needle body of the micro needle is conical or polygonal conical, preferably conical. When the microneedles form a microneedle array, the density of the microneedles is 25-1000 microneedles every square centimeter on the base. The height of the microneedle is 300-2000 μm, an angle of the microneedle tip is 10-90°, and the thickness of microneedle base is 10-500 μm.

In an example, in the needle tip, the mass ratio of the macromolecular material B to the biodegradable macromolecular material A which is difficultly soluble in water is 0.1:1-0.6:1. Controlling the ratio to be within said range, on the one hand, can well guarantee an improvement to the heat resistance of the needle tip so as to achieve storage and use in a high temperature environment, and on the other hand can well guarantee the strength and degradability of the biodegradable macromolecular material A.

In an example, the biodegradable macromolecular material A which is difficultly soluble in water is selected from one or more of PLA, PGA, PLGA, PCL, and derivatives thereof.

The macromolecular material B is selected from macromolecular materials that can be mixed with the biodegradable macromolecular material A to form a homogeneous system.

In an example, the glass transition temperature of the macromolecular material B is above 130° C.

In an example, the glass transition temperature of the macromolecular material B is above 150° C.

In an example, the macromolecular material B is selected from one or more of polyvinylpyrrolidone and derivatives thereof, and cellulose and derivatives thereof. These materials have better compatibility and mixing homogeneity with the biodegradable macromolecular material A which is difficultly soluble in water. The combination of both enables the needle tip to have better heat resistance, high strength, good puncture property, and degradation stability.

In an example, the needle tip further includes at least one active component. The term "active component" refers to a substance used for diagnosis, treatment, prevention, cosmetology, or health care, which is delivered in a transdermal manner using the microneedle or microneedle patch of the present application and has the efficacy of acting on animals or humans. According to the present application, the active component includes but is not limited to a pharmaceutical active component, a vaccine active component, a cosmetic active component, or a health care product active component, etc., which is selected according to actual needs.

In an example, the mass ratio of the sum of the biodegradable macromolecular material A and macromolecular material B to the active component is 0.5:1-1000:1, so as to ensure the mechanical strength and skin puncture property of the microneedle.

In an example, the needle tip further includes one or more a pore forming agent and a protective agent.

In an example, the pore forming agent can help intradermal water molecules enter a needle tip matrix to regulate a drug release rate. The pore forming agent includes but is not limited to one or more of sodium chloride, sodium carbonate, sodium bicarbonate, ammonium bicarbonate, polyvinylpyrrolidone, hyaluronic acid and sodium salt thereof, cellulose derivatives, trehalose, maltose, and cyclodextrins.

In an example, the amount of the added pore forming agent is 0.1%-20% of the total mass of the needle tip.

In an example, the protective agent includes but is not limited to one or more of polyhydroxy compounds (mannitol, sorbitol, or polyethylene glycol, etc.), carbohydrate compounds (trehalose, dextrin, lactose, or sucrose, etc.), serum albumin, polyvinylpyrrolidone, chondroitin sulfate, and amino acids (proline, tryptophan, glutamic acid, or glycine, etc.).

In an example, the amount of the added protective agent is less than 20% of the total mass of the needle tip.

In an example, the needle body and the base are independently formed from a matrix including a water-soluble macromolecular material.

In an example, the water-soluble macromolecular material is selected from one or more of carboxymethyl cellulose, hydroxypropyl methyl cellulose, hydroxyethyl cellulose, carboxymethyl chitosan, chitosan and derivatives thereof, polyvinyl alcohol and derivatives thereof, polyvinyl pyrrolidone and derivatives thereof, sodium hyaluronate, chondroitin sulfate, dextran and derivatives thereof, sodium alginate, poly γ-glutamic acid, pullulan, gelatin, polydopamine, or polyacrylamide.

In an example, the molecular weight of the water-soluble macromolecular material is 10-1000 kDa.

In order to achieve the second objective, the present application adopts the following technical solution:

A method for preparing a heat-resistant implantable polymer microneedle includes the following steps:

1) mixing a biodegradable macromolecular material A which has a glass transition temperature of 35-65° C. and is difficultly soluble in water and a portion of an organic solvent, adding a macromolecular material B, and optionally adding a pore forming agent and a protective agent to obtain a needle tip matrix solution; mixing an active component and the remainder of the organic solvent to obtain a drug solution; and mixing the drug solution and the needle tip matrix solution to obtain a needle tip injection molding solution; or mixing a biodegradable macromolecular material A which has a glass transition temperature of 35-65° C. and is difficultly soluble in water and an organic solvent, adding a macromolecular material B, optionally adding a pore forming agent and a protective agent, and adding an active component to obtain a needle tip matrix solution after mixing;

2) providing an injection molding solution of a needle body and a base; and 3) adding the needle tip injection molding solution to a microneedle mold so that the solution enters a mold cavity under vacuum, performing heating at 30-80° C., and volatilizing the organic solvent, so as to prepare the needle tip; and adding the injection molding solution of the needle body and the base to the microneedle mold so that the solution enters the mold cavity under vacuum, performing drying at the room temperature, and performing demolding, so as to prepare the heat-resistant implantable polymer microneedle.

In an example, the needle body and the base are integrally molded.

In an example, the injection molding solution of the needle body and the base is obtained by mixing a water-soluble macromolecular material with water.

In an example, the organic solvent is one or more of acetone, ethyl acetate, dichloromethane, dimethyl sulfoxide, N-methylpyrrolidone, and N, N-dimethylacetamide.

In order to achieve the third objective, the present application adopts the following technical solution:

A microneedle patch includes a microneedle array composed of microneedles as described in the first objective and a back lining.

In an example, the back lining is a pressure-sensitive adhesive back lining or a silicone back lining or a hydrocolloid.

A method for preparing the heat-resistant implantable polymer microneedle patch is implemented by preparing the microneedle array on the basis of the preparation of the heat-resistant implantable polymer microneedle, pasting the back lining on the back of a substrate of the microneedle array, and then performing demolding.

In order to achieve the fourth objective, the present application provides use of the microneedle patch in the fields of medicine, health care, and cosmetology.

The present application has the following beneficial effects:

In the technical solution of the microneedle provided by the present application, the addition of the macromolecular material B improves the heat resistance of the microneedle under the condition of ensuring good mechanical property and puncture property of the microneedle, achieving long-term stability in a high temperature environment (40-60° C. and above) without melting deformation, and thereby broadening conditions for storing and using, at high temperatures, the polymer microneedle containing the biodegradable macromolecular material which has a relatively low glass transition temperature and is difficultly soluble in water.

BRIEF DESCRIPTION OF THE DRAWINGS

The implementations of the present application are described in detail below with reference to the drawings.

DETAILED DESCRIPTION OF THE DISCLOSURE

Figure 1:
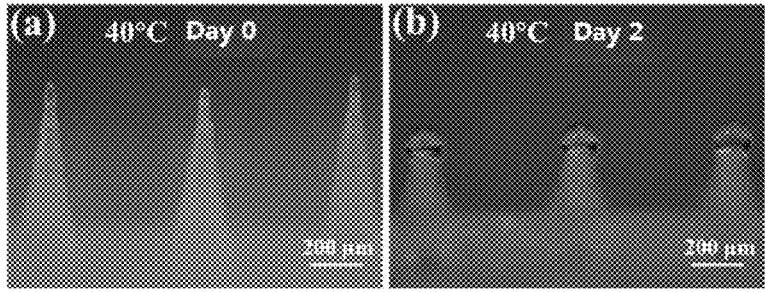
FIG. 1 shows side views of a microneedle at 40° C. on (a) Day 0 and (b) Day 2, wherein a needle tip formation is PLGA RG502.

In order to describe the present application more clearly, the present application is described below with reference to preferred embodiments and accompanying drawings. Similar components in the drawings are represented by the same reference numeral. Those skilled in the art should understand that the content specifically described below is illustrative rather than restrictive and should not limit the scope of protection of the present application.

Example 1

Preparation and Heat Resistance Evaluation of a Heat-Resistant Implantable Polymer Microneedle Patch Containing a Fluorescent Dye (1) A matrix solution containing 6% (w/w) PLGA (10 KDa, 50/50) and 0.2% (w/w) fluorescent bright-red dye (liposoluble analog drug) was prepared using N-methylpyrrolidone as a solvent, 30% (w/w) (w/w % of the PLGA mass) PVP K90 was added to the matrix solution, and the matrix solution was vortex-mixed and then used as a needle tip injection molding solution.

(2) A 20% (w/w) PVA solution was prepared by heating and swelling using water as a solvent and polyvinyl alcohol (PVA) as a matrix. A solution containing 20% (w/w) PVP K120 was prepared by swelling at the room temperature using water as a solvent and PVP K120 as a matrix. Then the two solutions were mixed with the mass ratio of PVA:PVP K120 being 1:2, a mixture solution was stirred to mix well, and then centrifugation was performed to remove bubbles, so as to obtain an injection molding solution of a needle body and a base.

(3) The needle tip injection molding solution was drawn and placed on a microneedle mold (the needle height is 700 μm, and the step height is 300 μm), the solution entered a mold cavity under vacuum, the redundant solution was removed, and the remaining solution was heated at 60° C. for 1 hour. Then 30 μL of injection molding solution of the needle body and the base was drawn and placed on the microneedle mold, vacuumizing was performed so that the solution entered the mold cavity, and the solution was dried for 2.5 h at the room temperature, a pressure-sensitive adhesive back lining was pasted on the back of the base, and then demolding was performed, so as to obtain the heat-resistant implantable polymer microneedle patch loaded with a fluorescent dye, having a needle tip height of 300 μm and a total needle height of 700 μm.

Figure 2:
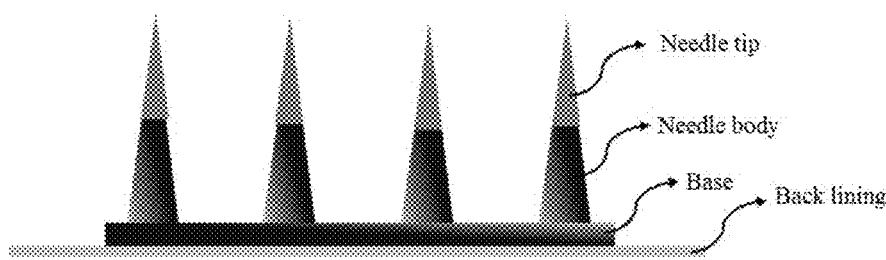
FIG. 2 shows a structural schematic diagram of a microneedle patch.
Figure 3:
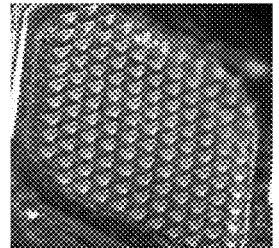
FIG. 3 shows a stereomicroscope photograph of a heat-resistant implantable polymer microneedle patch labeled with a fluorescent dye.
Figure 4:
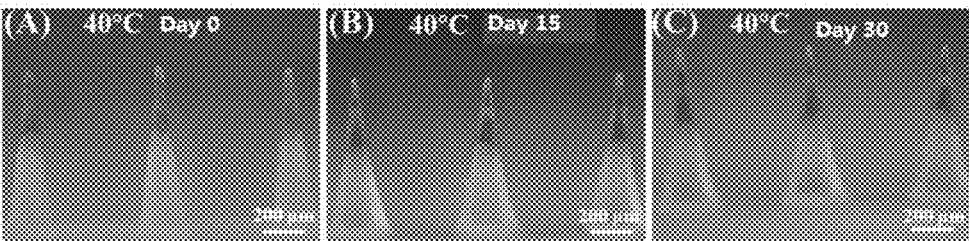
FIG. 4 shows side views of a heat-resistant implantable polymer microneedle labeled with a fluorescent dye at 40° C. on (A) Day 0, (B) Day 15, and (C) Day 30.

FIG. 2 shows a structural schematic diagram of the prepared polymer microneedle patch. Heat resistance evaluation: The prepared microneedle patch is shown in FIG. 3, where there are 117 microneedles on each microneedle patch. The microneedle was sealed and packaged and then placed in an incubator at 40° C. for one month, and was taken out at 0-th, 15-th, and 30-th days, and the side view of the microneedle was observed with an optical microscope. Results are shown in FIG. 4. It can be found that the morphology of the heat-resistant implantable polymer microneedle loaded with a fluorescent dye remained intact after the microneedle stood at 40° C. for one month, and the microneedle still has the puncture property when the ambient humidity exceeds 45% RH.

Example 2

Figure 5:
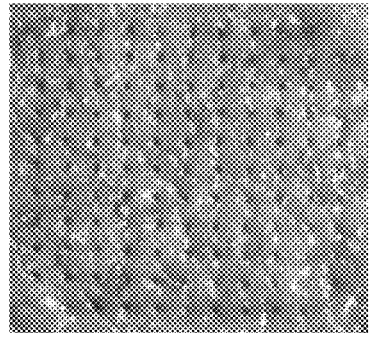
FIG. 5 shows a stereomicroscope photograph of a heat-resistant implantable polymer microneedle patch labeled with a fluorescent dye that punctures the skin of a pig ear.

Skin Puncture and Needle Tip Implantation Test of the Heat-Resistant Implantable Polymer Microneedle Patch The microneedle patch in example 1, which stood at 40° C. for one month, was applied to the skin of a fresh pig ear, pressed and held with a self-made needle feeder (30 N/cm2) for 20 s, then placed on agar hydrogel to moisturize for 20 min. Then the microneedle patch was peeled off, to observe, using a stereomicroscope, whether there is an implanted dyed needle tip in the pig ear skin. FIG. 5 shows an implantation photograph of the microneedle tip in the pig ear skin, and it can be clearly seen that the fluorescent bright-red needle tip is left in the skin, with a needle tip implantation rate close to 100%, indicating that the heat-resistant implantable polymer microneedle still has the skin puncture property after stood at 40° C. for one month.

Example 3

Preparation and Evaluation of Heat Resistance and In-Vitro Release of a Heat-Resistant Implantable Polymer Microneedle Patch Including a Difficultly-Soluble Drug (1) A matrix solution containing 4.8% (w/w) PLGA (10 KDa, 50/50) and 3.2% (w/w) levonorgestrel (LNG) was prepared using N, N-dimethylacetamide as a solvent, 0%, 20.0%, 25.0%, and 33.3% (w/w % of the PLGA mass) of hydroxypropyl methyl cellulose (HPMC, 15 cp) were added to the matrix solution respectively, and the matrix solution was vortex-mixed to obtain four needle tip injection molding solutions.

(2) A 25% (w/w) PVP K120 solution was prepared by swelling at the room temperature using water as a solvent and PVP K120 as a matrix, and used as an injection molding solution for the needle body and the base.

(3) The four needle tip injection molding solutions were drawn and placed on microneedle molds respectively, the solution entered mold cavity under vacuum, the redundant solution was removed, and the remaining solution was heated at 60° C. for 1 hour. Then 30 μL of injection molding solution of the needle body and the base was drawn and placed on the microneedle mold, vacuumizing was performed so that the solution entered the mold cavity, and the solution was dried for 2.5 h at the room temperature, a pressure-sensitive adhesive back lining was pasted on the back of the base, and then demolding was performed. The model of the microneedle mold used in this example is the same as that in Example 1. Each prepared microneedle patch includes 117 needles, and the total needle height is 700 μm.

The microneedle patch containing HPMC prepared in this example still has the puncture property when the ambient humidity exceeds 45% RH.

Figure 6:
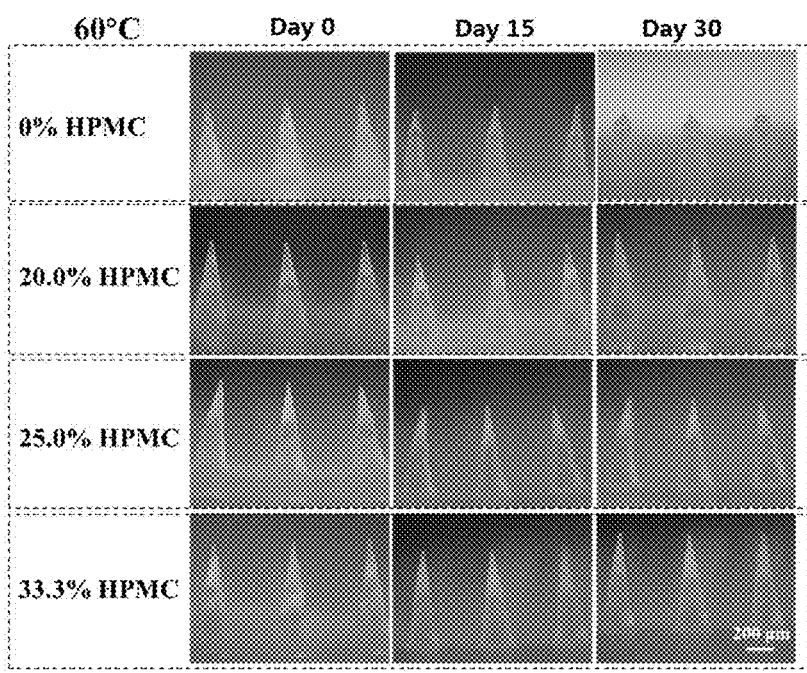
FIG. 6 shows side views of implantable polymer microneedles loaded with levonorgestrel in different formulations which stand at 60° C. for 0 days, 5 days, and 10 days.

Heat resistance evaluation: The prepared four types of microneedles were sealed and packaged and then placed in an incubator at 60° C. for 10 days, and were taken out at 0-th, 5-th, and 10-th days, and the side view of the microneedle was observed with an optical microscope. Results are shown in FIG. 6. It can be found that, the needle tip of the implantable polymer microneedle loaded with LNG containing no HPMC obviously melted and deformed after the microneedle stood at 60° C. for 10 days, while the morphologies of the drug-loaded heat-resistant implantable polymer microneedles containing different amounts of HPMC remained intact after the microneedles stood at 60° C. for 10 days.

Drug loading amount test: One piece of microneedle was placed into a centrifuge tube, 0.7 mL acetonitrile was added, then 0.3 mL ultrapure water was added after vortex dissolution, centrifugation was performed after vortex mixing, and centrifuged supernatant was analyzed by means of liquid chromatography. The drug loading amount tests were performed on the four types of microneedles respectively. In the tests, 5 microneedles were tested in parallel, and it was measured that the drug loading amount of each microneedle was 72±4.3 μg.

Figure 7:
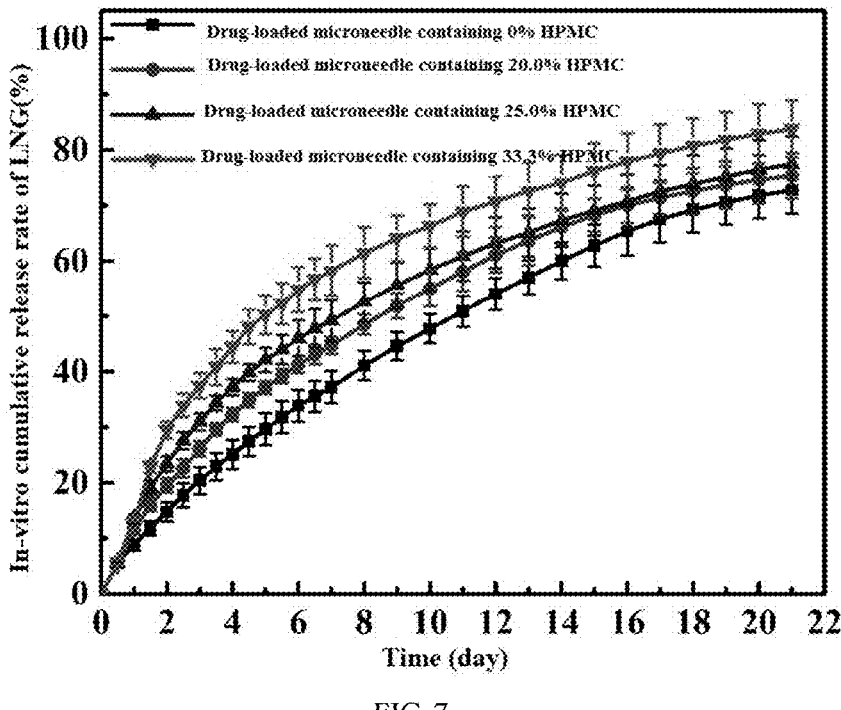
FIG. 7 shows in-vitro cumulative release curves of implantable polymer microneedles loaded with levonorgestrel in different formulations.

In-vitro release evaluation: The needle tip of the microneedle was scraped off with a scalpel and sealed in a dialysis bag, where a receptor fluid was 25% (v/v) ethanol-PBST. Samples were taken every 12 h in the first 7 days and every day in the next 14 days, where a sampling manner is total sampling, and the same amount of fresh receptor fluid was added. Drug concentration in the receptor fluid at each sampling point was measured by means of liquid chromatography, and results are shown in FIG. 7. It can be seen from the figure that the in-vitro cumulative release rates of the drug-loaded microneedles with needle tips containing 0%, 20.0%, 25.0%, and 33.3% (w/w % of the PLGA mass) of HPMC in 21 days were 72.8±4.3%, 75.3±4.0%, 77.5±4.9%, and 83.8±5.1%, respectively. With the increase of HPMC content in the needle tip, the cumulative release rate of LNG increases gradually, indicating that the addition of HPMC can not only enhance the heat resistance of the microneedle, but also help to improve the bioavailability of the difficultly-soluble LNG

Examples 4-8

Refer to Example 1 for a preparation method, where parameters of various components in Examples 4-8 are shown in Table 1.

TABLE 1

| | | | Proportions and Process Parameters of the Components | | |
|---|---|---|---|---|---|
| | Example 4 | Example 5 | Example 6 | Example 7 | Example 8 |
| Needle tip injection molding solution | 100 mg/mL PLGA (10 KDa, 75/25) + 10 mg/mL PVP K17 + 45 mg/mL leuprorelin acetate | 150 mg/mL PLA (25 KDa) + 20 mg/mL HPMC (30 cp) + 60 mg/mL etonogestrel | 80 mg/mL PLA (25 KDa) + 20 mg/mL hydroxypropyl cellulose (30 cp) + 40 mg/mL progesterone | 120 mg/mL PGA (20 KDa) + 36 mg/mL HPMC (15 cp) + 50 mg/mL p-nitroacetanilide | 90 mg/mLPCL (30 KDa) + 50 mg/mL hydroxybutylcellulose (15 cp) + 5 mg/mL norethisterone diacetate |
| Injection molding solution of the needle body and base | Total solid content is 40%, where carboxymethyl chitosan (50 KDa):PVP K90 is 1:1 | Total solid content is 30%, where PVA (6.0 cp):PVP K90 is 2:1 | Total solid content is 30%, where sodium carboxymethyl cellulose (200 KDa):dextran (70 kDa) is 1:1 | PVA (6.0 cp) solution with 25% solid content | Hydroxypropylmethylcellulose (50 cp) with 25% solid content |
| Heating temperature and time of the needle tip | 65° C., 1.5 h | 70° C., 1 h | 60° C., 1 h | 50° C., 1.5 h | 75° C., 0.5 h |

TABLE 1-continued

| | | Proportions and Process Parameters of the Components | | | |
|---|---|---|---|---|---|
| | Example 4 | Example 5 | Example 6 | Example 7 | Example 8 |
| Heat resistance of the microneedle | Stable storage at 40° C. for more than 0.5 month | Stable storage at 40° C. for more than 1 month | Stable storage at 40° C. for more than 2 months | Stable storage at 40° C. for more than 1.5 months | Stable storage at 40° C. for more than 3 months |
| Skin puncture property | Yes | Yes | Yes | Yes | Yes |

Microneedle patches prepared in Examples 4-8 still have the puncture property when the ambient humidity exceeds 45% RH.

It should be noted that the needle body and base in the above examples not only correspond to one example, but also can be combined with a needle tip in other examples, where the heating temperature and time of the needle tip and the heat resistance of the microneedle are determined by the composition of the needle tip injection molding solution.

Examples 9-14

Refer to Example 1 for a preparation method, where parameters of various components in Examples 9-14 are shown in Table 2.

aged microneedle was placed in an incubator at 40° C. for one month, and taken out at 0-th, 15-th, and 30-th days. It was found that the microneedle of this formulation lost the puncture property when the ambient humidity exceeds 45% RH.

Comparative Example 2

Example 1 was repeated, with a difference that the mass ratio of PLGA to PVP K90 in the needle tip is 1:0.05, where the other conditions remain unchanged, so as to prepare a microneedle and a microneedle patch. The sealed and packaged microneedle was placed in an incubator at 40° C. for one month, and taken out at 0-th, 15-th, and 30-th days. It

TABLE 1

| | | | Proportions and Process Parameters of the Components | | | |
|---|---|---|---|---|---|---|
| | Example 9 | Example 10 | Example 11 | Example 12 | Example 13 | Example 14 |
| Needle tip injection molding solution | 200 mg/mL PLGA (30 KDa, 85/15) + 32 mg/mL PVP K30 + 2 mg/mL Goserellin | 80 mg/mL PLGA (30 KDa, 65/35) + 30 mg/mL PVP K90 + 10 mg/mL diacerein | 100 mg/mL PGA (15 KDa) + 15 mg/mL hydroxypropylcellulose (15 cp) + 36 mg/mL Finasteride | 100 mg/mL PGA (15 KDa) + 15 mg/mL hydroxypropylcellulose (15 cp) + 15 mg/mL trehalose + 36 mg/mL Finasteride | 60 mg/mL PCL (25 KDa) + 8 mg/mL hydroxybutylcellulose (30 cp) + 2 mg/mL hydroxypropyl-β-cyclodextrin + 12 mg/mL Paliperidone | 45 mg/mL PLA (10 KDa) + 20 mg/mL HPMC (50 cp) + 18 mg/mL sucrose + 10 mg/mL Exenatide |
| Injection molding solution of the needle body and base | | | Total solid content is 25%, where PVA (6.0 cp):PVP K90 is 1:1 | | | |
| Heating temperature and time of the needle tip | 70° C., 0.5 h | 75° C., 0.5 h | 65° C., 1 h | 65° C., 2 h | 75° C., 1 h | 40° C., 3 h |
| Heat resistance of the microneedle | Stable storage at 60° C. for more than 15 days | Stable storage at 60° C. for more than 1 month | Stable storage at 50° C. for more than 10 days | Stable storage at 50° C. for more than 10 days | Stable storage at 50° C. for more than 1 month | Stable storage at 40° C. for more than 1 month |
| Skin puncture property | Yes | Yes | Yes | Yes | Yes | Yes |

Microneedle patches prepared in Examples 9-14 still have the puncture property when the ambient humidity exceeds 45% RH.

Comparative Example 1

Example 1 was repeated, with a difference that the mass ratio of PLGA to PVP K90 in the needle tip is 1:0.8, where the other conditions remain unchanged, so as to prepare a microneedle and a microneedle patch. The sealed and packwas found that the needle tip of the microneedle of this formulation fully melted and deformed after the microneedle stood at 40° C. for 15 days.

Comparative Example 3

Example 1 was repeated, with a difference that PVP K90 is replaced with HHPC, where the other conditions remain unchanged, so as to prepare a microneedle and a microneedle patch. The sealed and packaged microneedle was placed in an incubator at 40° C. for one month, and taken out at 0-th, 15-th, and 30-th days. It was found that the microneedle of this formulation has no puncture property.

Obviously, the above embodiments of the present application are only examples for clearly describing the present application rather than limiting the embodiments of the present application. Those of ordinary skilled in the art could make other different forms of changes or modifications on the basis of the above description. It is impossible to enumerate all the embodiments herein, and any obvious change or modification derived from the technical solution of the present application still falls within the scope of protection of the present application.

What is claimed is:

1. A heat-resistant implantable polymer microneedle, comprising a needle tip, a needle body, and a base, wherein the needle tip comprises a homogeneous system formed by mixing a biodegradable macromolecular material A which has a glass transition temperature of 35-65° C. and is substantially insoluble in water at 25° C. and a macromolecular material B having a glass transition temperature higher than that of the biodegradable macromolecular material A wherein the glass transition temperature of the macromolecular material B is above 130° C., and wherein, in the needle tip, a mass ratio of the macromolecular material B to the biodegradable macromolecular material A is 0.1:1-0.6:1.

2. The microneedle according to claim 1, wherein the biodegradable macromolecular material A is selected from one or more of PLA, PGA, PLGA, PCL, and derivatives thereof.

3. The microneedle according to claim 1, wherein the macromolecular material B is selected from one or more of polyvinylpyrrolidone and derivatives thereof, and cellulose and derivatives thereof.

4. The microneedle according to claim 1, wherein the needle tip further comprises at least one active component.

5. The microneedle according to claim 1, wherein the needle tip further comprises one or more a pore forming agent and a protective agent.

6. The microneedle according to claim 1, wherein the needle body and the base are independently formed from a matrix comprising a water-soluble macromolecular material.

7. A method for preparing a microneedle according to claim 1, comprising the following steps:

1) mixing the biodegradable macromolecular material A and a portion of an organic solvent, adding the macromolecular material B, and adding a pore forming agent and a protective agent to obtain a needle tip matrix solution; mixing an active component and the remainder of the organic solvent to obtain a drug solution; and mixing the drug solution and the needle tip matrix solution to obtain a needle tip injection molding solution; or Mixing the biodegradable macromolecular material A and an organic solvent, adding the macromolecular material B, optionally adding a pore forming agent and a protective agent, and adding an active component to obtain a needle tip matrix solution after mixing;

2) providing an injection molding solution of a needle body and a base; and 3) adding the needle tip injection molding solution to a microneedle mold so that the solution enters a mold cavity under vacuum, performing heating at 30-80° C., and volatilizing the organic solvent, so as to prepare the needle tip; and adding the injection molding solution of the needle body and the base to the microneedle mold so that the solution enters the mold cavity under vacuum, performing drying at the room temperature, and performing demolding, so as to prepare the heat-resistant implantable polymer microneedle.

8. A microneedle patch, comprising a microneedle array composed of microneedles according to claim 1 and a back lining.

9. Use of the microneedle patch according to claim 8 in the fields of medicine, health care, and cosmetology.

10. The microneedle according to claim 4, wherein the mass ratio of the sum of the biodegradable macromolecular material A and macromolecular material B to the active component is 0.5:1-1000:1.

11. The microneedle according to claim 5, wherein the amount of the added pore forming agent is 0.1%-20% of the total mass of the needle tip.

12. The micro needle according to claim 5, wherein the amount of the added protective agent is less than 20% of the total mass of the needle tip.

13. The microneedle according to claim 11, wherein the amount of the added protective agent is less than 20% of the total mass of the needle tip.

14. The microneedle according to claim 6, wherein the water-soluble macromolecular material is selected from one or more of carboxymethyl cellulose, hydroxypropyl methyl cellulose, hydroxyethyl cellulose, carboxymethyl chitosan, chitosan and derivatives thereof, polyvinyl alcohol and derivatives thereof, polyvinyl pyrrolidone and derivatives thereof, sodium hyaluronate, chondroitin sulfate, dextran and derivatives thereof, sodium alginate, poly γ-glutamic acid, pullulan, gelatin, polydopamine, or polyacrylamide.

15. The microneedle of claim 6, wherein the molecular weight of the water-soluble macromolecular material is 10-1000 kDa.

16. The microneedle of claim 14, wherein the molecular weight of the water-soluble macromolecular material is 10-1000 kDa.

* * * * *